United States Patent
Ahotupa et al.

(10) Patent No.: US 7,005,447 B2
(45) Date of Patent: *Feb. 28, 2006

(54) FOOD PRODUCT COMPRISING HYDROXYMATAIRESINOL

(75) Inventors: Markku Ahotupa, Turku (FI); Christer Eckerman, Turku (FI); Lauri Kangas, Lieto (FI); Sari Mäkelä, Turku (FI); Niina Saarinen, Merimasku (FI); Risto Santti, Naantali (FI); Anni Wärri, Lieto (FI)

(73) Assignee: Hormos Nutraceutical Oy Ltd., Turku (FI)

( * ) Notice: Subject to any disclaimer, the term of this patent is extended or adjusted under 35 U.S.C. 154(b) by 310 days.

This patent is subject to a terminal disclaimer.

(21) Appl. No.: 10/639,530

(22) Filed: Aug. 13, 2003

(65) Prior Publication Data

US 2004/0048804 A1    Mar. 11, 2004

Related U.S. Application Data

(63) Continuation of application No. 09/972,850, filed on Oct. 10, 2001, now Pat. No. 6,689,809, which is a continuation-in-part of application No. 09/829,944, filed on Apr. 11, 2001, now abandoned, which is a continuation of application No. 09/281,094, filed on Mar. 30, 1999, now Pat. No. 6,451,849.

(51) Int. Cl.
*A61K 31/34* (2006.01)
*A23L 1/30* (2006.01)
(52) U.S. Cl. ..................... 514/461; 426/648
(58) Field of Classification Search ............... 426/648; 514/461

See application file for complete search history.

(56) References Cited

U.S. PATENT DOCUMENTS 4,808,574 A * 2/1989 Brekhman et al. ............ 514/23
5,554,258 A * 9/1996 Suess et al. .................. 162/24
5,846,944 A * 12/1998 Prasad .......................... 514/25
6,271,257 B1 * 8/2001 Mutanen ..................... 514/461

FOREIGN PATENT DOCUMENTS

DE          3641495 A1     6/1988
WO       WO 97/14670     4/1997
WO       WO 97/32593     9/1997

OTHER PUBLICATIONS

Davin et al., "Lignans in Chemoprevention Against the Onset of Breast and Prostate Cancers: Origins of the 'Mammalian' Lignans, Enterodiol and Enterolactone," *Third Tannin Conference*, (Jul. 1998).

Fukuda et al., "Antioxidants Obtained from Sesame Seeds for Pharmaceutical Products and Food Additives," C.A. 132:310001 (2000) (Abstracting Japanese Patent Application 2000-129256).

Ford et al., "Plant Lignans and Health: Cancer Chemoprevention and Biotechnological Opportunities," *Plant Polyphenols 2: Chemistry, Biology, Pharmacology, Ecology* 675-694 (Sep. 1999).

Mattinen et al., "NMR-spectroscopic Study of Hydroxymatairesinol, the Major Lignan in Norway Spruce (*Picea abies*) Heartwood," 135 *Models in Chemistry* 583-590 (1998).

Kuridze et al., Izv. Akad. Nauk Gruz. SSR, Ser. Khim., (1981) vol. 7, No. 3, pp. 213-223 (Abstract).

* cited by examiner

*Primary Examiner*—Rebecca Cook
(74) *Attorney, Agent, or Firm*—James C. Lydon

(57) ABSTRACT

A food product containing an effective amount of an active agent which is hydroxymatairesinol, a geometric isomer or stereoisomer thereof, or an acceptable salt thereof, or a mixture thereof, where the food product is selected from the group consisting of a nutritional supplement and a nutrient. The food product can increase the level of enterolactone or another metabolite of hydroxymatairesinol in a person's serum thereby causing prevention of a cancer or a certain non-cancer, hormone dependent disease in a person, based on the administration of hydroxymatairesinol to the person.

2 Claims, 5 Drawing Sheets

Estrogenic and antiestrogenic activity of HMR in MCF-7 cells. The cell proliferation of control is adjusted to 100 %.
Number of experiments, n = 3-4.

\* Significantly different from control

A = control (vehicle without hormones)
B = vehicle + estradiol $10^{-9}$M
C = vehicle + HMR $10^{-6}$M
D = vehicle + HMR $10^{-6}$M + estradiol $10^{-9}$M Relative uterus weight (mg/kg body weight) of immature rats treated with HMR or MPV-2213ad.

\* Significantly different from control

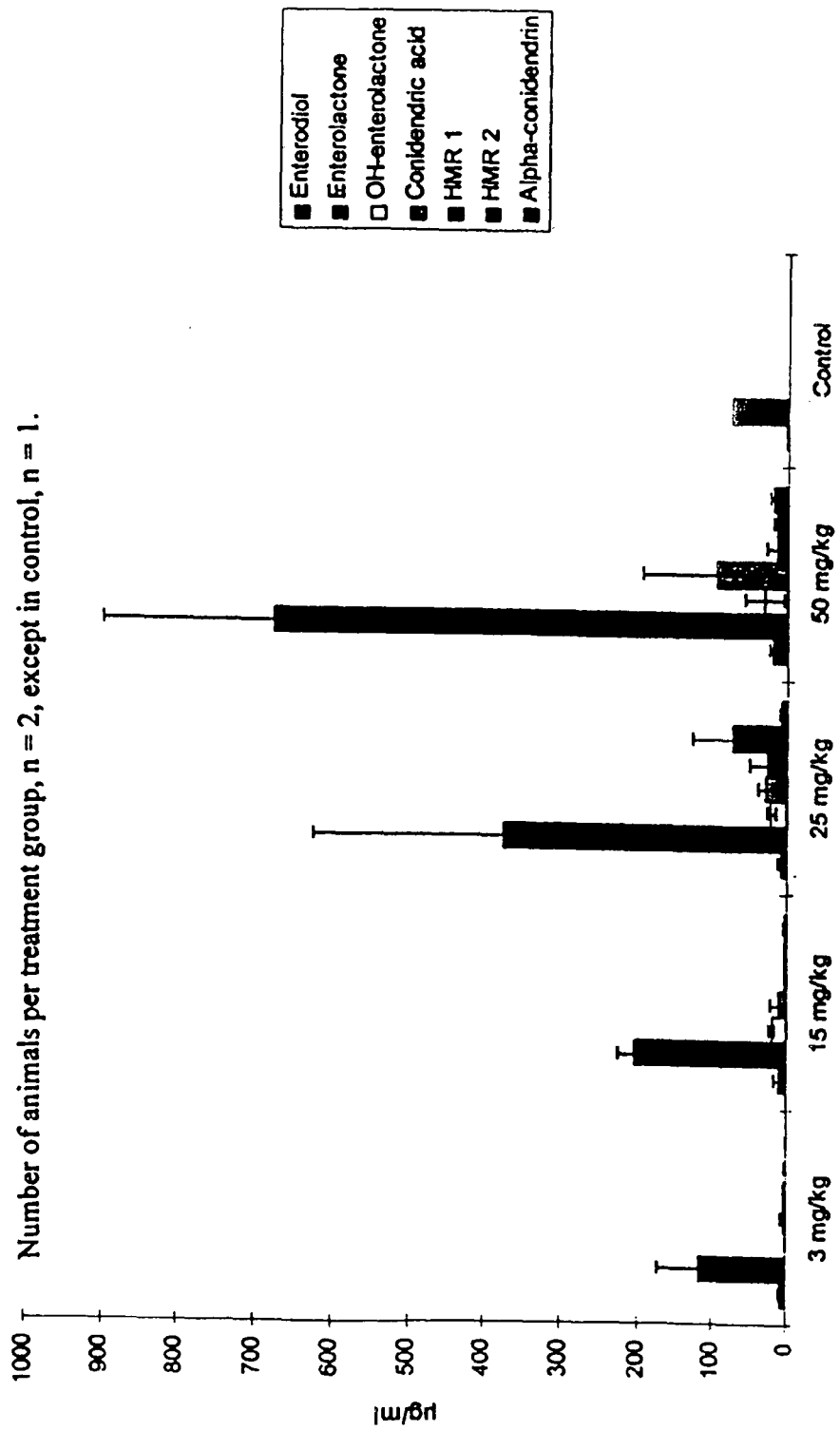

FOOD PRODUCT COMPRISING HYDROXYMATAIRESINOL

This application is a continuation of application Ser. No. 09/972,850, filed Oct. 10, 2001, now U.S. Pat. No. 6,689,809, which is a continuation in part of application Ser. No. 09/829,944, filed Apr. 11, 2001 and now abandoned, which is a continuation of application Ser. No. 09/281,094, filed Mar. 30, 1999 and now U.S. Pat. No. 6,451,849.

FIELD OF THE INVENTION

This invention relates to methods for prevention of cancers, certain non-cancer, hormone dependent diseases and/or cardiovascular diseases in a person, based on administering of hydroxymatairesinol to said person. The invention also concerns a method for increasing the level of enterolactone or another metabolite of hydroxymatairesinol in a person's serum thereby causing prevention of a cancer or a certain non-cancer, hormone dependent disease in a person, based on administering of hydroxymatairesinol to said person. Furthermore, this invention relates to pharmaceutical preparations, food additives and food products comprising hydroxymatairesinol.

BACKGROUND OF THE INVENTION

The publications and other materials used herein to illuminate the background of the invention, and in particular, cases to provide additional details respecting the practice, are incorporated by reference.

Lignans are defined as a class of phenolic compounds possessing a 2,3-dibenzylbutane skeleton. They are formed by coupling of monomeric units called precursors such as cinnamic acid, caffeic, ferulic, coumaric, and gallic acids (Ayres and Loike, 1990). Lignans are widely distributed in plants. They can be found in different parts (roots, leafs, stem, seeds, fruits) but mainly in small amounts. In many sources (seeds, fruits) lignans are found as glycosidic conjugates associated with fiber component of plants. The most common dietary sources of mammalian lignan precursors are unrefined grain products. The highest concentrations in edible plants have been found in flaxseed, followed by unrefined grain products, particularly rye. Mammalian lignan production from different plant food are given in Table 1.

Considerable amounts of lignans are also found in coniferous trees. The type of lignans differs in different species and the amounts of lignans vary in different parts of the trees. The typical lignans in heart wood of spruce (*Picea abies*) are hydroxymatairesinol (HMR), α-conidendrin, conidendrinic acid, matairesinol, isolariciresinol, secoisolariciresinol, liovile, picearesinol, lariciresinol and pinoresinol (Ekman 1979). The far most abundant single component of lignans in spruce is HMR, about 60 per cent of total lignans, which occurs mainly in unconjugated free form. Lignan concentration in thick roots is 2–3 per cent. Abundance of lignans occur in the heart wood of branches (5–10 per cent) and twists and especially in the knots, where the amount of lignans may be higher than 10 per cent (Ekman, 1976 and 1979). These concentrations are about hundred-fold compared to ground flax powder known as lignan-rich material.

The chemical structure of hydroxymatairesinol is

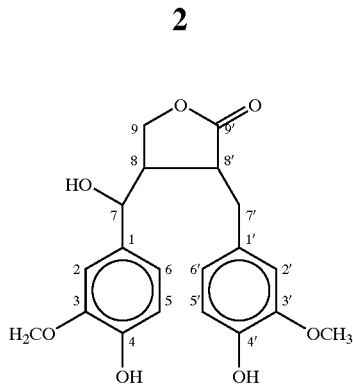

Lignans can be isolated e.g. from compression-wood fiber. These fibers originate from compression wood of stems and knots (oversize chip fraction) worsen the quality of paper (Ekman, 1976).

Plant lignans such as matairesinol and secoisolariciresinol, are converted by gut microflora to mammalian lignans, enterolactone and enterodiol, correspondingly (Axelson et al. 1982). They undergo an enterohepatic circulation and are excreted in the urine as glucuronide conjugates (Axelson and Setchell, 1981). As an experimental evidence for the chemopreventive actions of lignans, supplementation of a high-fat diet with lignan-rich flaxseed flour (5% or 10%) or flaxseed lignans (secoisolariciresinol-diglycoside, SDG) prevented the development of antiestrogen-sensitive DMBA-induced breast cancer in the rat (Serraino and Thompson 1991 and 1992; Thompson et al. 1996a and 1996b). They reduced the epithelial cell proliferation, nuclear aberrations, the growth of tumors, and the development of new tumors. High lignan intake may also protect against experimental prostate and colon cancers. Dietary rye (containing lignans), prevented at early stages the growth of transplanted Dunning R3327 prostatic adenocarcinomas in rats (Zhang et al. 1997; Landström et al. 1998). The percentage of animals bearing palpable tumors, the tumor volume, and the growth rate were significantly lower. Further, flaxseed or SDG supplementation inhibited the formation of chemically induced aberrant crypts in rat colon (Serraino and Thompson 1992; Jenab and Thompson 1996). The antitumor action may therefore be due to weak estrogen-antiestrogen-like properties and/or other mechanisms, which are not well understood.

Urinary excretion and serum concentrations of enterolactone are low in women diagnosed with breast cancer (Ingram et al. 1997; Hultén et al. 1998) suggesting that lignans are chemopreventive. Mammalian lignans (enterolactone and enterodiol) have been hypothesized to modulate hormone-related cancers, such as breast cancer, because of their structural similarities to the estrogens. Enterolactone had weak estrogenic potency in MCF-7 cells (Mousavi and Adlercreutz 1992), but had no estrogenic response in mouse uterine weight (Setchell et al. 1981). As a sign of estrogen-like activity, SDG feeding during pregnancy and lactation to rats increased the uterine weight at weaning but the effect was not evident at later stages (Tou et al. 1998). Possible antitumor effects have also been associated with their antiestrogenic actions (Waters and Knowler, 1982). The inhibition of aromatase by mammalian lignan, enterolactone, would suggest a mechanism by which consumption of lignan-rich plant food might contribute to reduction of estrogen-dependent diseases, such as breast cancer (Adlercreutz et al. 1993, Wang et al. 1994). The potential antioxidant activity of lignans could also represent a mechanism associated with the preventive action of lignans in the development of cancers. Further, mammalian lignans have shown to inhibit the conversion of testosterone to 5α-dihydrotestosterone (DHT), the potent intracellular androgen, at the concentrations which are achievable in humans (Evans et al. 1995). The reduction in DHT concentration would modify the risk of prostate cancer (PC) and benign prostatic hyperplasia (BPH).

It is possible that lignans as precursors of enterolactone could also alleviate lower urinary tract symptoms (LUTS) and gynecomastia. On the basis of the results obtained in the animal model, we have suggested that estrogens play an essential role in the development of the muscular dysfunction involved in urethral dyssynergia seen as bladder neck dyssynergia or external sphincter pseudodyssynergia (Streng et al. unpublished observations). Such neuromuscular changes are at least partially reversed by an aromatase inhibitor (MPV-2213ad) indicating the role of estrogens. Further, gynecomastia, which is induced by exposure to estrogens or in the presence of increased ratio of estrogen to androgens. Gynecomastia can be successfully treated with an aromatase inhibitor. The capability of lignans to inhibit 5α-reductase and/or aromatase combined with their potential antioxidant activity may represent mechanisms associated with the preventive action of lignans in the development of hormone-related diseases in male organism.

No data is available on the possible effects of lignans in humans. The current theories about lignan action in humans have been derived from studies on the effects of diets supplemented with flaxseed products (and thus lignans). Flaxseed in human female diet caused changes in menstrual cycle (Phipps et al. 1993). The subjects, all normally cycling women, showed a longer mean length of luteal phase and higher progesterone/17β-estradiol ration in serum during the luteal phase when they took 10 g of flax seed powder/day in addition to their habitual diets (Phipps et al. 1993). No significant differences between flax and control cycles or concentrations of either estrone or 17β-estradiol were found. Neither there were any significant differences between flax and control groups for concentrations of serum estrogens in postmenopausal women (Brzezinski et al. 1997). Flaxseed supplementation increased SHBG (protein which binds estradiol with high capacity) concentration in serum. This is a typical estrogenic effect in the liver tissue. Increased SHBG concentration on the other hand reduces bioavailability of endogenous estrogens. In healthy young men, the short-term (6 weeks) flaxseed supplementation of the diet (10 g/d in muffins) had no significant effect on plasma testosterone concentrations (Shultz et al. 1991) indicating a lack of estrogenicity in the male organism. All together, these studies indicate that lignans may have weak hormonal (estrogenic and antiestrogenic) effects, but the mechanism of their action cannot be fully described by the hormonal effects.

In conclusion, isolated mammalian lignans have not been available earlier in sufficient amounts to be used in animal experiments or clinical trials, and the only possibility to increase lignan intake has been to increase the consumption of fiber-rich food items such as flaxseed. HMR or any other lignan that is efficiently converted to enterolactone, and can be produced/isolated in large quantities would be valuable in the development of pharmaceutical preparations and food products such as functional foods for chemoprevention of cancer and other hormone-related diseases and cardiovascular diseases.

SUMMARY OF THE INVENTION

According to one aspect, this invention concerns a method for prevention of a cancer, a certain non-cancer, hormone dependent disease and/or a cardiovascular disease in a person comprising administering to said person an effective amount of hydroxymatairesinol, a geometric isomer or a stereoisomer thereof, or a salt thereof.

According to an other aspect, the invention concerns a method for increasing the level of enterolactone or another metabolite of hydroxymatairesinol in a person's serum thereby causing prevention of a cancer or a certain non-cancer, hormone dependent disease in a person comprising administering to said person an effective amount of hydroxymatairesinol, a geometric isomer or a stereoisomer thereof, or a salt thereof.

According to a third aspect, the invention concerns a pharmaceutical preparation comprising an effective amount of hydroxymatairesinol, a geometric isomer or a stereoisomer thereof, or a pharmaceutically acceptable salt thereof, in combination with a pharmaceutically acceptable carrier.

According to a fourth aspect, the invention concerns a product comprising hydroxymatairesinol, a geometric isomer or a stereoisomer thereof, or a salt thereof, in combination with a solid or liquid carrier, for use as additive to a food product.

According to a fifth aspect, the invention concerns a food product comprising an effective amount of hydroxymatairesinol, a geometric isomer or a stereoisomer thereof, or a salt thereof.

According to still one aspect, the invention concerns a method for increasing the stability of a food product comprising the addition to said food product of an effective amount of hydroxymatairesinol, a geometric isomer or a stereoisomer thereof, or a salt thereof.

BRIEF DESCRIPTION OF THE DRAWINGS

FIG. 5 shows the excretion of enterolactone in the urine of rats treated with different doses of HMR.

DETAILED DESCRIPTION OF THE INVENTION

Figure 1:
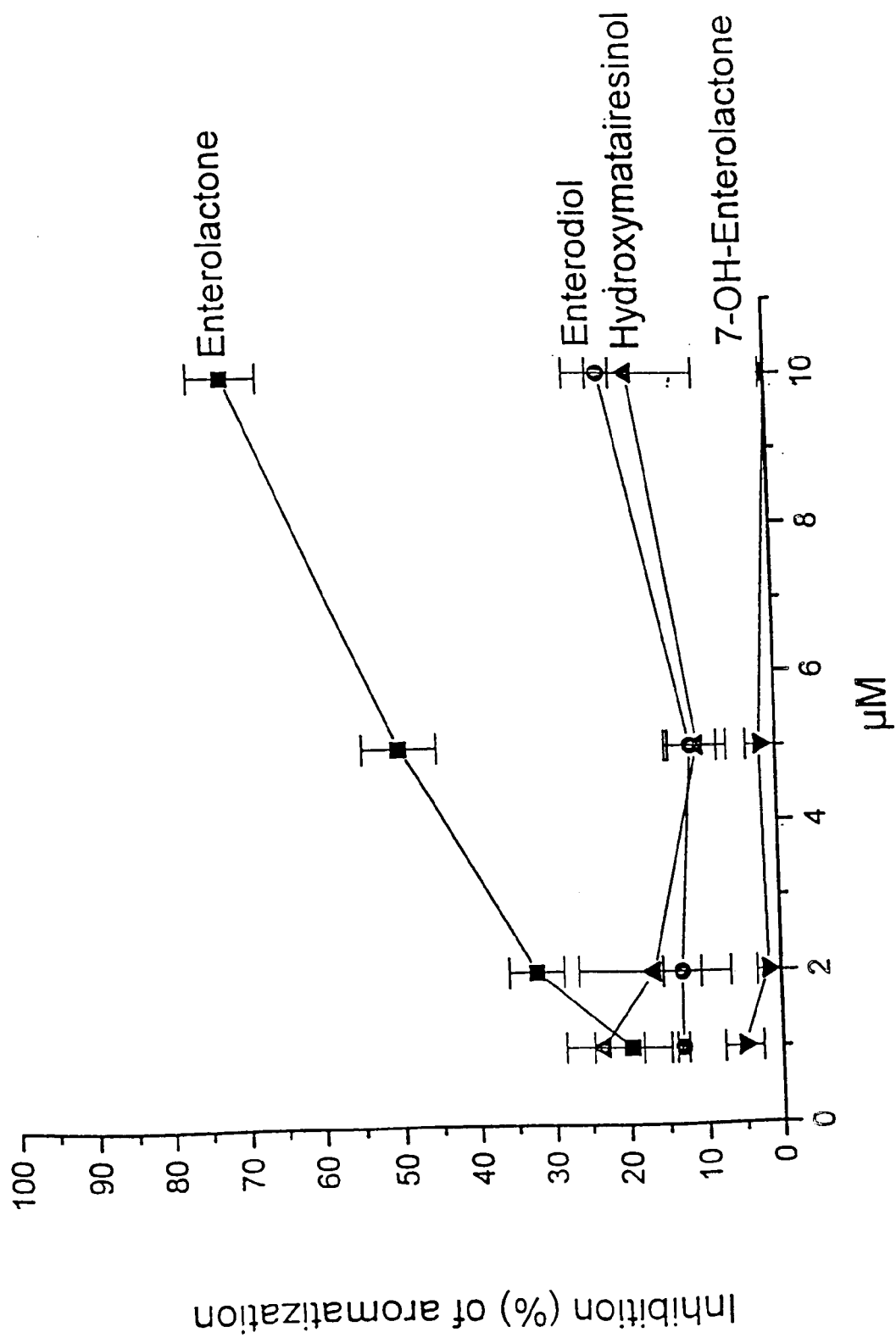
FIG. 1 shows the concentration-related inhibition of aromatase by lignans in JEG-3 cells.

This invention relates to the use of a lignan, hydroxymatairesinol (HMR), for the prevention of cancer, non-cancer, hormone dependent diseases and cardiovascular diseases by adding said HMR into food or by using it as a pharmaceutical preparation. Surprisingly, HMR is metabolized in vivo to enterolactone, which is assumed to account at least partly for the antitumor properties of the lignans. Antioxidative activity of HMR in vitro is strong and this property indicates that HMR can also prevent cardiovascular diseases through the protective effect against damaging free oxygen species in the body. The invention relates also to the use of HMR as a food additive to increase the food stability (i.e. inhibit lipid and pigment oxidations and vitamin losses which cause loss of nutritional value and development of off-flavors in food).

The method according to this invention is particularly effective in the prevention of cancers such as breast cancer, prostate cancer and colon cancer, non-cancer, hormonal dependent diseases such as lower urinary tract symptoms, urethral dyssynergia, bladder instability, bladder outlet obstruction, benign prostatic hyperplasia, and gynecomastia in men, and cardiovascular diseases resulting from oxidized LDL in serum.

The pharmaceutical preparation according to this invention is preferably an oral formulation. The required amount of the active compound (HMR) will vary with the particular condition to be prevented. A typical dose ranges from about 10 to about 100 mg per day and adult person. Typical dosage forms include, but are not limited to, oral dosage forms such as powders, granules, capsules, tablets, caplets, lozenges, liquids, elixirs, emulsions and suspensions. All such dosage forms may include conventional carriers, diluents, excipients, binders and additives known to those skilled in the medicinal and pharmaceutical arts.

The pharmaceutical carriers typically employed may be solid or liquid. Thus, for example, solid carriers include polysaccharides such as lactose, sucrose, gelatin, agar, while liquid carriers include aqueous solutions of salts, polysaccarides, complexing agents, surfactants, syrups, vegetable oils such as peanut oil or olive oil, and certain alcohols. However, any pharmaceutically acceptable solid or liquid carrier can be used in the pharmaceutical preparation according to the invention, except that the formulation cannot be a mixture of only the active agent and plain water.

In the food additive of the invention, the carrier to be used, can be any non-toxic solid or liquid carrier acceptable for use in food and suitable to be admixed with HMR without affecting the properties of HMR. The role of the material is mainly to make the exact dosage of HMR easier. A suitable concentration is for example 100 mg to 1 g of HMR per 100 g of carrier. Typical dosage forms include, but are not limited to, oral dosage forms such as powders, granules, capsules, tablets, caplets, lozenges, liquids, elixirs, emulsions and suspensions. All such dosage forms may include conventional carriers, diluents, excipients, binders and additives known to those skilled in the art.

Typical solid carriers include polysaccharides such as lactose, sucrose, gelatin, agar, while liquid carriers include aqueous solutions of salts, polysaccharides, complexing agents, surfactants, syrups, vegetable oils such as peanut oil or olive oil, and certain alcohols. However, any acceptable solid or liquid carrier can be used in the food additive according to the invention, except that the food additive formulation cannot be a mixture of only the active agent and plain water.

The food product according to this invention is especially a functional food, a nutritional supplement, a nutrient, a pharmafood, a nutraceutical, a health food, a designer food or any food product. A suitable concentration of HMR in the food product is, for example, 1 to 20 mg of HMR per 100 g of food product.

The functional food according to this invention can, for example be in the form of butter, margarin, biscuits, bread, cake, candy, confectionery, yogurt or an other fermented milk product, or cereal such as muesli.

The addition of hydroxymatairesinol is particularly useful to increase food stability in the meaning of inhibitition of lipid, vitamin and pigment oxidations, which cause loss of nutritional value and development of off-flavors in food. A suitable concentration of HMR for this purpose is, for example, about 0.1%.

Isolation of HMR for use in this invention can be made from oversize chip fraction (containing branches, twists and knots) of compression wood. According to a preferred embodiment, the hydroxymatairesinol is derived from coniferous wood. It has been shown that hydroxymatairesinol is the dominant lignin in coniferous wood. For example, in knotrich spruce wood 85% or even more of the lignins is hydroxymatairesinol.

The properties of HMR were studied by seven different assays:
1. Measurement of antioxidant capacity in vitro
2. Measurement of aromatase inhibiting capacity in JEG-3 cells
3. Measurement of estrogenic and antiestrogenic activity in MCF-7 cell cultures
4. Evaluation of estrogenic and antiestrogenic activity by uterine growth bioassay
5. Measurement of estrogenic and antiestrogenic activity in adult male rats
6. Investigating the antitumor activity in rat DMBA-induced mammary cancer model
7. Analysis of metabolites from rat urine after different doses of HMR The isolation and purification of HMR in sufficient amounts for biological tests has been impossible earlier because it is a component of wood lignans, which have been relatively poorly characterized. Understanding the distribution of HMR in different parts of spruce (Ekman 1976 and 1979) has given the opportunity to study lignans and especially HMR in detail.

A linear correlation was found between the doses of HMR and the amounts of urinary enterolactone. Enterolactone is a well known mammalian lignan formed by intestinal bacteria from matairesinol or by oxidation of enterodiol (Axelson and Setchell 1981; Axelson et al. 1982). Only minute amounts of unmetabolized HMR and other metabolites (enterodiol and 7-hydroxyenterolactone) were found in urine. Their amounts remained unchanged when the daily dose of HMR was increased. These findings suggest that HMR was metabolized to enterolactone, and, further, enterolactone derived from HMR through demethylation and dehydroxylation steps is not converted to enterodiol. Based on the structure of HMR one had expected that 7-hydroxyenterolactone were the main metabolite of HMR, but this was not the case. This hydroxyl group is eliminated in the metabolism. The metabolism of HMR differs from that of SDG. SDG is metabolized to enterodiol which is partly oxidized to enterolactone (Rickard et al. 1996; Lampe et al. 1994). HMR thus offers an advantage over SDG as a direct precursor of enterolactone.

Figure 2:
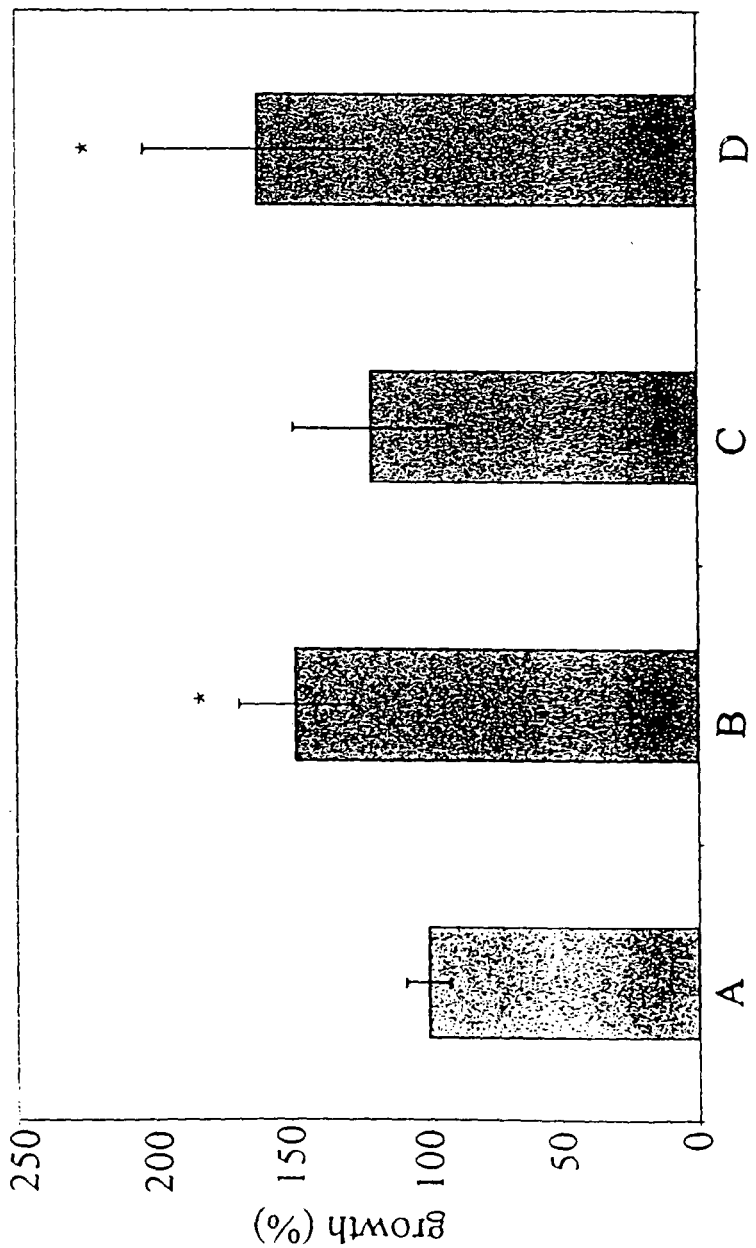
FIG. 2 shows the proliferation of MCF-7 cells in the presence and absence of HMR.

HMR had weak if any estrogenic action in rat uterus or in the male organism. It exerted weak but not significant estrogen-like activity in MCF-7 cells. No antiestrogenic activity was demonstrated for HMR. Therefore, it is surprising that it had highly significant antitumor activity in DMBA-induced tumor model in rats as shown in FIG. 2. The activity of HMR may be due to HMR itself or to enterolactone. However, no dose-dependence was found in the chemopreventive action of HMR when given in two different doses (3 and 15 mg/kg) to rats after DMBA-treatment. Thus HMR needs not to be converted to enterolactone to have an antitumor effect or smaller doses of these lignans are sufficient to accomplish the maximal chemopreventive effects.

HMR is very effective antioxidant as shown in Tables 2 and 3. It is one of the most potent known inhibitors of lipid peroxidation and excellent inhibitor of LDL oxidation. Inhibition of LDL oxidation is considered to be of special importance in humans as the concentration of oxidized LDL in serum is considered to be one of the best predictors of cardiovascular diseases such as atherosclerosis. HMR may serve as a food additive to increase the food stability (i.e. inhibit vitamin, lipid and pigment oxidations which cause loss of nutritional value and development of off-flavors in food), because HMR was much better superoxide anion scavenging and peroxyl radical scavenging agent than well known antioxidants butylated hydroxyanisol (BHA) and butylated hydroxytoluene (BHT), which are commonly used for increasing the food stability.

Experiments

Chemicals

Various lignans were tested in vitro for their estrogenicity, antiestrogenicity, capability to inhibit aromatization and for their antioxidative properties. The test compounds were purchased from the following sources: enterodiol and enterolactone from Plantech, London, UK, and 7-hydroxyenterolactone containing two 7-OH enantiomers was a generous gift from Dr. Kristina Wähälä, Department of Applied Chemistry, University of Helsinki, Finland.

Extraction of HMR from Wood

HMR extracts were isolated from Norway spruce (Picea abies) as described by Ekman, 1976 and Ekman 1979. Shortly, freeze-dryed ground heartwood was Soxhlet-extracted in with hexane to remove non-polar lipophilic extractive. The wood sample was re-extracted in the same apparatus with acetone/water (9:1 v/v) to give crude lignans. Hydroxymatairesinol (HMR) and its isomer were isolated and re-chromatographed with XAD-resin for further purification.

Measurement of Antioxidant Capacity In Vitro

The antioxidative capacity of lignans was estimated by four different methods: 1) inhibition of lipid peroxidation, 2) inhibition of low density lipoprotein (LDL) oxidation, 3) superoxide anion scavenging and 4) peroxyl radical scavenging assays.

Inhibition of lipid peroxidation was evaluated on the basis of their potency to inhibit tert-butylhydroperoxide-induced lipid peroxidation (t-BuOOH-LP) in rat liver microsomes in vitro (Ahotupa et al. 1997). The test for the t-BuOOH-LP was carried out as follows: The buffer (50 mM sodium carbonate, pH 10.2, with 0.1 mM EDTA) was pipetted in a volume of 0.8 ml in the luminometer cuvette. Twenty microliters of diluted liver microsomes, final concentration 1.5 mg protein/ml, was added, followed by 6 ml of luminol (0.5 mg/ml) and test chemicals. The test compounds were added to incubation mixtures in a small volume diluted in ethanol or dimethylsulphoxide (2% of incubation volume), and the lipid peroxidation potency was compared to that of the vehicle (ethanol or dimethyl sulphoxide). The reaction was initiated by 0.05 ml of 0.9 mM t-BuOOH at 33° C. Chemiluminescence was measured for about 45 min at 1 min cycles, and the area under curve (integral) was calculated. Chemiluminescence measurements were carried out using a Bio-Orbit 1251 Luminometer (Bio-Orbit, Turku, Finland) connected to a personal computer using dedicated software for the assays.

Inhibition of LDL oxidation was estimated as described by Ahotupa et al, 1996. Shortly: LDL was isolated by precipitation with buffered heparin. After resuspendation in phosphate buffer, 20 mM $CuCl_2$ was added and the mixture was incubated for 3 hrs at +37° C. After this, LDL lipids were extracted with chloroform-methanol, dried under nitrogen, redissolved in cyclohexane and analyzed spectrophotometrically at 234 nm. The intensity of absorbance is indicative of LDL oxidation. To test the ability of different compounds to prevent LDL oxidation, the compounds were added to the incubation mixture prior addition of $CuCl_2$. Possible interference of test compounds with the assay procedure was excluded by measuring the absorption at 234 nm before and after the incubation period. For those compounds which showed antioxidative potency at the starting concentration (0,1 mM), IC-50 values (i.e. concentrations at which test compound inhibited LDL oxidation by 50%) was determined.

Superoxide anion scavenging method was based on the superoxide anion produced in controlled conditions by xanthine-xanthine oxidase system and detection of the generated reactive oxygen species by luminometer (Ahotupa et al., 1997). The ability of test compounds to decrease the chemiluminescence was evaluated. IC-50 concentration (concentration which prevented the chemiluminescence by 50%) was calculated.

Peroxyl radiocal scavenging assay was based on generation of peroxyl radicals by thermal decomposition of 2,2'-azobis(2-amidinopropane)HCl and their detection by chemiluminescence (Ahotupa et al., 1997). The results were calculated as the stochiometric factor, i.e. how many moles of peroxyl radicals can be scavenged by one mole of the test compound.

Measurement of Aromatase Inhibiting Capacity in JEG-3 Cells

The effects of HMR and structurally related lignans (enterolactone, enterodiol and 7-hydroxyenterolactone) were studied on formation of $^3H$-17β-estradiol from $^3H$-androstenedione in JEG-3 cells, human choriocarcinoma cell line. The JEG-3 choriocarcinoma cells are a useful aromatase model enabling the study of aromatase inhibition in vitro (Krekels et al 1991). Cells were maintained in DMEM containing 10% fetal calf serum (FCS). The incubation mixture contained 50 μl $^3H$-androst-4-ene, 3,17-dione (0.5 nM), 50 μl unlabelled androstenedione (0.5 nM), 100 μl test compounds (10 mM) and 800 μl cell suspension (1 million cells). After the incubation for 4 h, unlabelled carriers (androstenedione, testosterone, 17β-estradiol and estrone) were added. The steroids were extracted twice with 3.0 ml dichloromethane. HPLC was used for separation and quantification of the radiolabelled $^3H$-17β-estradiol as previously described (Mäkelä et al. 1995). The column system consisted of a guard column followed by a C18 150×3.9 mm ID analytical column (Technopak 10 C18 HPLC Technology; Wellington House, Cheshire, UK). The mobile phase was acetonitrile/water (35/65) and the flow rate was 1.2 ml/min. For in-line detection of the radioactive metabolites, the eluent of the HPCL column was continuously mixed with liquid scintillant and then monitored with in-line radioactivity detector.

Measurement of Estrogenic and Antiestrogenic Activity in MCF-7 Cell Cultures

The MCF-7 cell line (human breast cancer cells) stock cultures were grown in phenol red free RPMI medium supplemented with 5% FCS, 100 U/ml penicillin and 100 μg/ml streptomycin, 10 μg/ml insulin and 1 nM 17β-estradiol in T-75 cell culture bottles. The medium was replaced with fresh ones three times per week. The stock cultures were harvested by trypsinization and suspended in 10 ml phenol red free versene solution and cenitifuged for 5 min 800 rpm. The cell pellet was carefully resuspended into RPMI medium supplemented with 5% dextran charcoal stripped FCS (dcFCS) and seeded on 6 well plates 50 000 cells/3.0 ml medium/well. On the second day of culture the medium was changed and test compounds were added. To test the estrogenicity of the lignan compounds, they were diluted in ethanol and added to cell cultures in final concentration of 1.0 M. In each proliferation assay 1.0 nM 17β-estradiol solution in ethanol was used as a positive control for estrogenic response. Equal amounts of ethanol were added to control wells. To test the antiestrogenicity both 17β-estradiol and lignan solutions were added to cell cultures. The cells were cultured for 5 to 7 days in the presence of test compounds, and the medium was changed every second day. Cell proliferation was quantified by counting the released nuclei with Coulter counter.

Evaluation of Estrogenic and Antiestrogenic Activity in Immature Rat Uterotropic Test The estrogenicity HMR was evaluated by the uterotropic assay in immature rats which was performed as described earlier (Jordan et al. 1977), with the exception of treatment time which was 7 days instead of 3 days in the reference study. The treatment time was longer because of the expected weak estrogenicity of the test compound. The treatment of immature rats with an aromatase inhibitor (MPV-2213 ad), which prevents biosynthesis of estradiol, was used as a methodological control for non-estrogen-stimulated uterus.

Evaluation of Estrogenic and Antiestrogenic Activity in Adult Male Rats

Estrogenic (antiandrogenic) and antiestrogenic effects of HMR were studied in intact and hypoandrogenic Noble strain male rats (age 6–9 month), correspondingly. The chronic hypoandrogenic state with both structural and functional changes in the male reproductive tract was induced by neonatal estrogenization (diethylstilbestrol, 10.0 μg/kg body weight in rape oil s.c. on postnatal days 1–5). These changes are known to be partly reversible by aromatase inhibitor treatment consisting daily dose of MPV- 2213 ad 10–30 mg/kg body weight (Streng et al. unpublished observations).

Animals were fed the soy-free basal diet (SDS, Whitham Essex, England) and they had a free access to water. Twelve of both intact and hypoandrogenic animals were cavaged in daily dosage of HMR 50 mg/kg body weight in rape oil. Another twelve animals from both animal models were cavaged with rape oil only as a placebo treatment. After four-week treatment the animals were sacrificed. The weights of testis and accessory sex glands (ventral prostate, seminal vesicles and coagulating gland) were measured. Serum and testis testosterone and pituitary and serum luteinizing hormone (LH) levels were measured by immunoassays (Haavisto et al. 1993).

Investigating the Antitumor Activity in Rat DMBA-induced Mammary Cancer Model

Antitumor activity of HMR in rat mammary cancer was studied as described earlier (Kangas et al. 1986). Fifty-day-old female Sprague-Dawley rats were given 12.0 mg DMBA (dimethylbentz[a]anthracene) by cavage. After approximately 6 weeks palpable tumors could be detected, whereafter the width (w) and the length (l) of the tumors were measured once a week to determine the tumor volumes according to a formula $V=(\pi w^2 l)/12$. The rats were also weighed once a week. The rats were allocated in 3 different groups so that the total number of tumors in the beginning of the experiment was similar in each group: (1) Control group 8 animals, (2) HMR 3.0 mg/kg 7 animals, and (3) HMR 15.0 mg/kg 7 animals, one of which had to be killed before the end of the experiment.

HMR was given per os starting 9 weeks after the DMBA-induction, i.e. 3 weeks after palpable tumors appeared, and was given daily for 7.5 weeks. At the end of the experiment the tumors were classified in groups according to their growth pattern: 1. Growing tumors (PD=progressive disease); 2. Non-growing, stabilized tumors (SD=stabilized disease, no change in tumor volume or regression less than 75%; 3. Regressing tumors (PR=partial response, regression of tumor volume more than 75%); 4. Disappeared tumors (CR=complete response, no palpable tumor).

Analysis of Metabolites from Rat Urine Receiving Different Doses of HMR

Ten Sprague—Dawley male rats (age 4 month) were used to study the metabolism of HMR in vivo. Animals were housed in pairs with 12 h light:dark cycle and had free access to water and soy-free basal diet (SDS, Whitham Essex, England) during the metabolism study.

Rats were cavaged with HMR dissolved in 10% ethanol in PEG in doses 3, 15, 25 and 50 mg/kg body weight once a day for two days. After second cavaging the 24 hour urine was collected in metabolic cages in collection jars containing 120 μl 0.56 M ascorbic acid and 120 μl 0.15 M Na-azide as preservatives. The centrifuged urine volumes were measured and stored in −20° C. For pretreatment 750 μl 0.2 M acetate buffer (pH 4.0±0.1) was added to 3.0 ml thawed urine aliquots. Sep-Pak C18 columns (100 mg silica based resin/column) were used for urine extractions. Columns were preconditioned with 3.0 ml $H_2O$, 3.0 ml methanol and 3.0 ml acetate buffer. After urine had filtered through the column and washed with 3.0 ml of acetate buffer polyphenolics were eluted with 3.0 ml methanol. The eluate was evaporated to dryness under nitrogen in +45° C. water bath and dryed residues were redissolved in 3.0 ml of 0.2 M acetate buffer. 30 μl Helix pomatia enzyme mix was added and the solutions were incubated in +37° C. to hydrolyze both glucuronides and sulfates. 300 μl of flavone stock solution (100 μg/ml in EtOH) was added into hydrolyzed samples. The samples were extracted in C-18 columns and evaporated to dryness as described above and stored in −20° C. until analyzed with GC-MS.

The evaporated urine samples were dissolved in pyridine, and silylated by adding BSTFA:TMCS (10:1) silylation reagent. The GC-MS analyses of the silylated samples were performed with an HP 6890-5973 GC-MS instrument. The GC column was an HP-1 crosslinked methyl polysiloxane column (15 m×0.25 mm i.d., 0.25 μm film thickness). Helium was used as carrier gas at a flow of 1 ml/min. The GC-oven was temperature programmed from 60° C. to 290° C., at 8° C./min heating rate. The GC-injector was set in split-mode at a split ratio of 1:15. The injector temperature was 250° C. Compound identifications were based on mass spectra. The quantitative calculations were based on uncorrected peak areas of target components relative to the internal standard.

Results

Assessment of Antioxidant Capacity In Vitro

HMR had stronger lipid peroxidation capacity than any other lignan or flavonoid in our tests (Table 2). HMR was compared to well known antioxidants TROLOX, which is a water soluble vitamin E derivative, and BHA and BHT in the ability of inhibiting lipid peroxidation, inhibition of LDL oxidation, and scavenging superoxide and peroxyl radicals (Table 3). HMR was as a whole the strongest antioxidant, more effective than BHA or BHT in all assays, and stronger than TROLOX in all assays except for lipid peroxidation inhibition assay, where the compounds were almost equally active.

Aromatase Inhibiting Capacity in JEG-3 Cells

The inhibition of $^3H$-17β-estradiol formation from $^3H$-androstenedione in JEG-3 cells was tested at different concentrations of HMR. The inhibitory capacity of HMR was compared to enterolactone, 7-hydroxyenterolactone and enterodiol. Enterolactone caused a dose-dependent inhibition of aromatization within the concentration range of 1.0 to 10.0 µM. It was further shown that enterodiol was noninhibitory indicating that the lactone ring is critical for the inhibition. 7-hydroxyenterolactone and hydroxymatairesinol had no inhibitory effects (FIG. 1) indicating the importance of the number and location hydroxyl groups in the lignan molecule for the aromatase inhibition.

Estrogenic and Antiestogenic Activity in MCF-7 Cell Cultures

HMR had very weak, not statistically significant estrogenic or antiestrogenic activity in MCF-7 cell proliferation assays as shown in FIG. 2.

Figure 3:
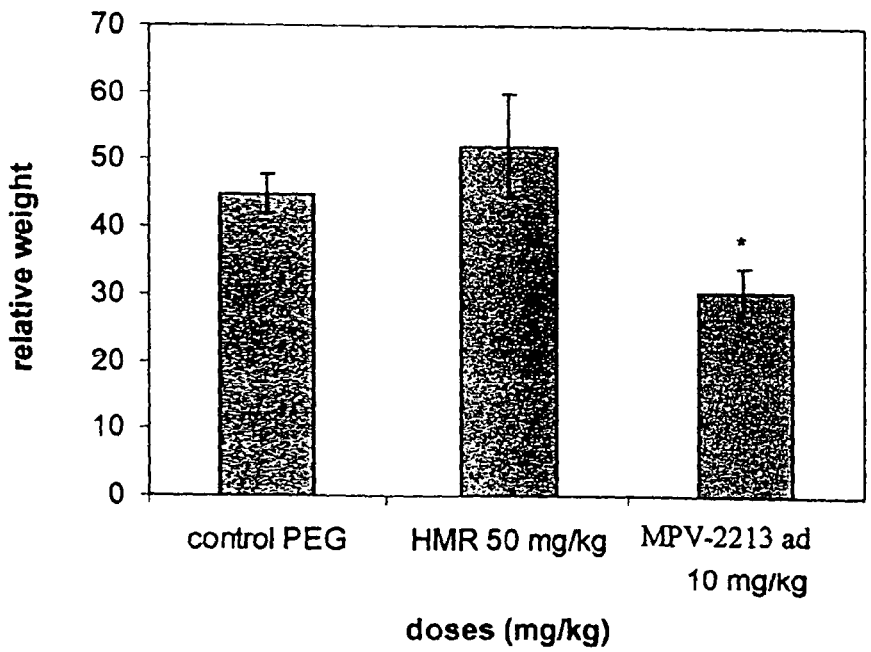
FIG. 3 shows the uterine wet weight of immature rats treated with HMR or with an aromatase inhibitor.

Evaluation of Estrogenic and Antiestrogenic Activity in Immature Rat Uterotropic Test FIG. 3 illustrates the effects of HMR on the uterine growth of the immature rats. HMR had no significant estrogenic effect on the uterine weight gain of the immature rats. Neither did HMR reduce the weight gains indicating no antiestrogenic effect. Aromatase inhibitor prevented the increase of uterine weight, as expected, indicating that the method for the measurement of the aromatase inhibitors was adequate.

Evaluation of Estrogenic and Antiestrogenic Activity in Adult Male Rats

After a 4-week treatment with HMR, no significant changes in the weights of accessory sex glands and testis were observed in control and hypoandrogenic animals (Table 4). There were no significant changes in testosterone or LH concentrations, either (Table 5). These results indicate, that HMR is not a full estrogen agonist in male organism, because it does not exert the typical estrogenic activity on hypothalamus—hypophysis—gonad—axis (inhibition of LH and androgen secretion). Neither is HMR an antiestrogen because it does not reverse the changes induced by neonatal estrogenization in the male rat.

Investigating the Antitumor Activity in Rat DMBA Induced Mammary Cancer Model

Figure 4:
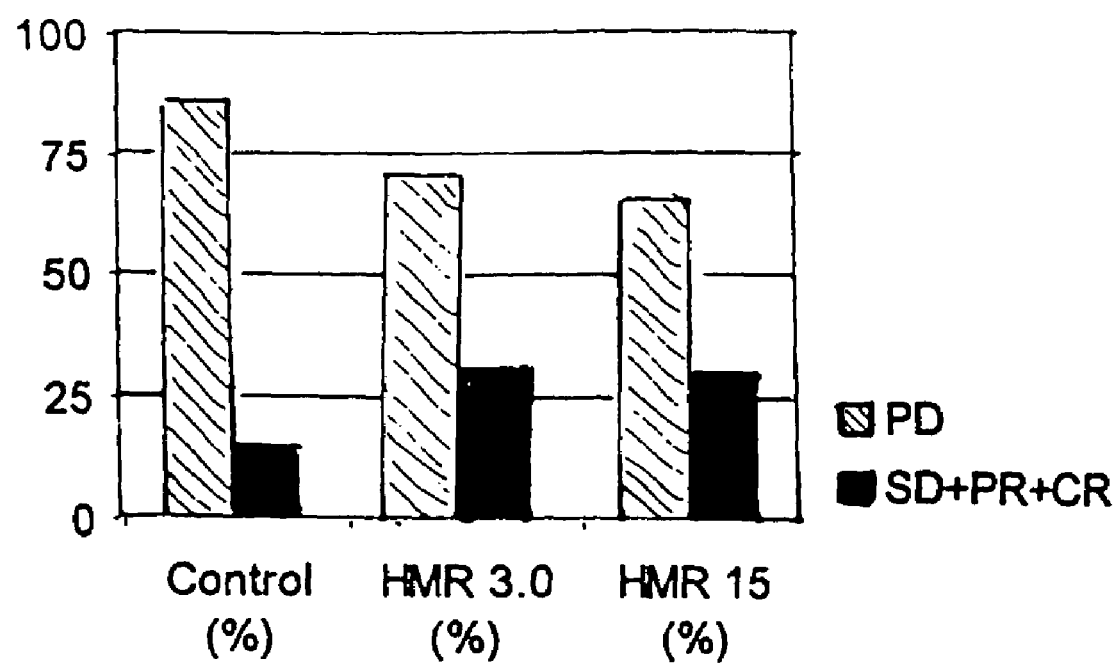
FIG. 4 shows the antitumor activity of HMR against DMBA-induced mammary gland tumors in female rats.

Number of growing (PD) versus stable (SD) tumors, regressing (PR) tumors and disappeared (CR) tumors is presented in FIG. 4. The antitumor effect of HMR was found to be statistically very significant. There was no clear dose-dependency of antitumor action in this model. Both antioxidative and tumor growth regressing properties of HMR may therefore be connected with the in vivo antitumor activity. The mechanism of antitumor activity of HMR in vivo is still unknown.

Analysis of Metabolites from Rat Urine After Different Doses of HMR

FIG. 5 illustrates that the main excreting metabolite of HMR in rats is enterolactone, which may be the biologically active compound. This is surprising taking into account the chemical structure of HMR, because one would expect hydroxyenterolactone to be the main metabolite. The metabolism of HMR to enterolactone may be catalyzed by bacterial intestinal flora rather than by the rat liver.

CONCLUSIONS

Hydroxymatairesinol (HMR) has antitumor activity either as unchanged compound and/or after conversion to enterolactone in DMBA induced breast cancer model. HMR has therefore a potential to have beneficial effects in humans who are at risk of developing breast cancer (BC), prostate cancer (PC), colon cancer or benign prostatic hyperplasia (BPH). HMR is metabolized to enterolactone which inhibits aromatization in vitro. HMR may as a precursor of aromatase inhibitor also prevent the development of lower urinary tract symptoms (LUTS), bladder instability, bladder outlet obstruction, urethral dyssynergia, and gynecomastia. HMR has also strong antioxidative activity and may therefore be used as food additive (antioxidant). HMR as pharmaceutical product or dietary supplement may have advantageous cardiovascular effects in humans. Addition of HMR to food to make innovative new functional food, nutraceutical, health food, pharmafood, designer food or novel food is feasible.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

TABLE 1

Production of mammalian lignans from different plant food by in vitro fermentation with human fecal flora.

|  | µg/100 g |
|---|---|
| FLAXSEED FLOUR | 68000 |
| SOYBEAN | 170 |
| CEREAL BRANS: |  |
| WHEAT | 570 |
| OAT | 650 |
| WHOLE CEREALS: |  |
| RYE | 160 |
| POTATO | 80 |
| CARROT | 350 |
| ONION | 110 |

[1]Thompson et al. Nutrition and Cancer 16:43–52, 1991

TABLE 2

ANTIOXIDANT PROPERTIES OF LIGNANS AND SOME RELATED FLAVONOIDS IN VITRO BY LIPID PEROXIDATION INHIBITION TEST.

| Compound | Antioxidative capacity (t-BuOOH-LP) $IC_{50}$ (µM) |
|---|---|
| Flavonoids |  |
| kaempferol (3,4',5,7-tetrahydroxy-flavone) | 0.9 |
| quercetin (3,3',4',5,7-pentahydroxy-flavone) | 0.4 |
| kaempferide (3,5,7-trihydroxy-4'-methoxy-flavone) | 0.5 |
| Lignans |  |
| enterolactone 2,3-bis-(3'-hydroxybenzyl)-butyrolactone | 15.9 |

TABLE 2-continued

ANTIOXIDANT PROPERTIES OF LIGNANS AND SOME RELATED FLAVONOIDS IN VITRO BY LIPID PEROXIDATION INHIBITION TEST.

| Compound | Antioxidative capacity (t-BuOOH-LP) $IC_{50}$ ($\mu M$) |
|---|---|
| enterodiol | 12.7 |
| 2,3-bis-(3'-hydroxybenzyl)-butane-1,4-diol hydroxymatairesinol | 0.08 |

TABLE 3

COMPARISON OF ANTIOXIDATIVE EFFECTS OF HMR AND KNOWN ANTIOXIDANTS IN VITRO. IC-50 concentrations have been presented, except for peroxyl radical scavenging assay where the stochiometric factor (i.e. how many moles of peroxyl radical one mole of test compound can scavenge).

|  | HMR[1] | TROLOX[2] | BHA[3] | BHT[4] |
|---|---|---|---|---|
| Inhibition of lipid peroxidation | 0.06 $\mu M$ | 0.02 $\mu M$ | 1.1 $\mu M$ | 15.3 $\mu M$ |
| Inhibition of LDL oxidation | 2.0 $\mu M$ | 2.7 $\mu M$ | not determined | |
| Superoxide anion scavenging | 5.6 $\mu M$ | 25 $\mu M$ | 15 $\mu M$ | >1 mM |
| Peroxyl radical scavenging | 1:4 | 1:2 | not determined | |

[1] hydroxymatairesinol
[2] water soluble E-vitamin derivative
[3] Butylated hydroxyanisol (synthetic antioxidant)
[4] Butylated hydroxytoluene (synthetic antioxidant)
Determination methods have been described in the text.

TABLE 4

The effect of four week exposure to HMR on male rat reproductive organ relative weights[1]

|  | Treatment | n | Body weight g | Testis | Ventral Prostate | Seminal vesicle | Coaculating gland |
|---|---|---|---|---|---|---|---|
|  |  |  |  |  | mg/kg body weight | | |
| Intact animals | Placebo | 12 | 426 ± 28 | 4362 ± 170 | 909 ± 146 | 412 ± 43 | 223 ± 49 |
|  | HMR 50 mg/kg | 12 | 447 ± 38 | 4223 ± 304 | 938 ± 148 | 419 ± 59 | 204 ± 48 |
| Hypoandrogenemic animals | Placebo | 12 | 481 ± 29 | 3340 ± 509 | 333 ± 188 | 249 ± 63 | 69 ± 49 |
|  | HMR 50 mg/kg | 12 | 455 ± 36 | 3276 ± 327 | 378 ± 198 | 266 ± 49 | 70 ± 30 |

[1] Data is expressed as mean ± SD (mg/kg body weight). Relative weights after HMR treatment are not significantly different from placebo in either group.

TABLE 5

The effect of four week exposure to HMR on male rat testosterone and LH concentrations[1]

|  | Treatment | n | Testis testosterone (ng/testis) | Serum testosterone (ng/ml) | Pituitary LH ($\mu g$/pit) | Serum LH (ng/ml) |
|---|---|---|---|---|---|---|
| Intact animals | Placebo | 12 | 97.6 ± 46.3 | 2.405 ± 1.122 | 6.747 ± 2.479 | 1.804 ± 1.294 |
|  | 50 mg/kg HMR | 12 | 112.9 ± 58.5 | 2.770 ± 1.421 | 6.838 ± 2.061 | 1.088 ± 0.352 |
| Hypoandrogenic animals | Placebo | 12 | 63.5 ± 25.9 | 1.197 ± 0.663 | 8.673 ± 2.224 | 0.712 ± 0.371 |
|  | 50 mg/kg HMR | 12 | 48.0 ± 15.2 | 0.939 ± 0.431 | 7.530 ± 2.286 | 0.854 ± 0.333 |

[1] Data is expressed as mean ± SD. Hormone concentrations after HMR treatment are not significantly different from placebo in either group.

References

Adlercreutz H, Bannwart C, Wähälä K, Mäkelä T, Brunow G, Hase T, Arosemena P J, Kellis J T, and Vickery L E: Inhibition of human aromatase by mammalian lignans and isoflavonoid phytoestrogens. J Steroid Biochem Mol Biol, 44: 147–153, 1993.

Ahotupa M, Ruutu M, and Mañtylä E: Simple methods of quantifying oxidation products and antioxidant potential of low density lipoproteins. Clin Biochem, 29: 139–144, 1996.

Ahotupa M, Mäntylä E, and Kangas L: Antioxidant properties of the triphenylethylene antiestrogen drug toremifene. Naunyn-Schmiedeberg's Arch Pharmacol, 356: 297–302, 1997.

Axelson M and Setchell K D R: The excretion of lignans in rats—evidence for an intestinal bacterial source for this new group of compounds. FEBS lett, 123: 337–342, 1981.

Axelson M, Sjövall J, Gustafsson B E and Setchell K D R: Origin of lignans in mammals and identification of a precursor from plants. Nature, 298: 659–660, 1982.

Ayres D, and Loike, J. Lignans: Chemical, bilogical and clinical properties. Cambridge university press, 1990.

Brzezinski A, Adlercreutz H, Shaoul R, Rösler A, Shmueli A, Tanos V and Schenker JG: Short-term effects of phytoestrogen-rich diet on postmenopausal women. Menopause (The Journal of the North American Menopause Society), 4: 89–94, 1997.

Ekman R: Analysis of lignans in Norway spruce by combined gas chromatography-mass spectrometry. Holztorschung, 30:79–85, 1976.

Ekman R: Distribution of lignans in Norway spruce. Acta Academiae Aboensis, Ser B, 39:1–6, 1979.

Evans B A, Griffiths K and Morton M S. Inhibition of 5α-reductase in genital skin fibroblasts and prostate tissue by dietary lignans and isoflavonoids. J Endocrinol, 147: 295–302, 1995.

Haavisto A-M, Petterson K, Bergendahl M, Perheentupa A, Roser J F, and Huhtaniemi I A. Supersensitive immunofluorometric assay for rat luteinizing hormone. Endocrinology, 132: 1687–1691, 1993.

Hultén K, Adlercreutz H, Winkvist A, Lenner P, Hallmans G and Ågren Å. Low levels of phyto-estrogens in blood as risk factor for breast cancer. In: COST 916 Workshop 'Phyto-oestrogens: exposure, bioavailability, health benefits and safety concerns', 1998

Ingram D, Sanders K. Kolybaba M and Lopez D. Case-control study of phyto-oestrogens and breast cancer. Lancet, Oct 4;350(9083): 990–994, 1997.

Jenab M and Thompson L U. The influence of flaxseed and lignans on colon carcinogenesis and beta-glucuronidase activity. Carcinogenesis, Jun;17(6): 1343–1348, 1996

Jordan V C, Collins M M, Rowsby L, Prestwich G: A monohydroxylated metabolite of tarnoxifen with potent antiestrogenic activity. J Endocrinol, 75: 305–316, 1977.

Kangas L, Nierminen A-L, Blanco G, Gronroos M, Kalijo S, Karjalainen A, Perilä M, Södervall M and Toivola R: A new triphenylethylene compound, Fc-1157a. II Antitumnor effects. Cancer Chemother Pharmacol, 17:109–113, 1986.

Lampe J W, Martini M C, Kurzer M S, Adlercreutz H and Slavin J L: Urinary lignan and isoflavonoid excretion in premenopausal women consuming flaxseed powder. Am J Clin Nutr, 60:122–8, 1994.

Landstrom M, Zhang J X, Halkmans G, Aman P, Bergh A, Damber J E, Mazur W, Wähälä K and Adlercreutz H. Inhibitory effects of soy and rye diets on the development of Dunning R3327 prostateadenocarcinoma in rats. Prostate, Aug 1; 36(3): 151–161, 1998

Mousavi Y and Adlercreutz H: Enterolactone and estradiol inhibit each other's proliferative effect on MCF-7 breast cancer cells in culture. J Steroid Biochem Mol Biol, 41: 615–619, 1992.

Mattinen J, Sjöholm R and Ekman R. NMR-spectroscopic study of hydroxymatairesinol, the major lignan in Norway spruce (Picea abies) heartwood. ACH models in chemistry, 135(4):583–590, 1998.

Mäkelä S, Poutanen M, Lehtimäki J, Kostian M-L, Santti R and Vihko R. Estrogen-specific 17β-hydroxysteroid oxidoreductase type 1 (E.C.1.1.1.62) as a possible target for the action of phytoestrogens. P.S.E.B.M., 208:51–59, 1995.

Phipps W R, Martini M C, Lampe J W, Slavin J L and Kurzer M S. Effect of flax seed ingestion on the menstrual cycle. J Clin Endocrinol Metab, 77(5):1215–1219, 1993.

Rickard S E, Orcheson L J, Seidl M M, Luyengi L, Fong H H S and Thompson L U: Dose-dependent production of mammalian lignans in rats and in vitro from the purified precursor secoisolariciresinol diglycoside in flaxseed. J Nutr, 126: 2012–2019, 1996.

Shultz T D, Bonorden W R and Seaman W R. Effect of short-time flaxseed consumption on lignan and sex hormone metabolism in men. Nutrition Research, 11:1089–110, 1991.

Serraino M and Thompson L U: The effect of flaxseed supplementation on early risk markers for mammary carcinogenesis. Cancer Letters, 60: 135–142, 1991.

Serraino M and Thompson L U: The effect of flaxseed supplementation on the initiation and promotional stages of mammary tumorigenesis. Nutr Cancer, 17:153–159, 1992.

Setchell K D R, Borriello S P, Gordon H, Lawson A M, Harkness R and Morgan D M L. Lignan formation in man—microbial involvement and possible roles in relation to cancer. Lancet, 4:4–7, 1981

Streng T, Talo A and Santti R. Unpublished observations. Thompson L U, Robb P, Serraino M and Cheung F. Mammalian lignan production from various foods. Nutr Cancer, 16: 43–52, 1991

Thompson L U, Seidl, M M, Rickard S E, Orcheson, L J, and Fong H H S: Antitumorigenic effect of a mammalian lignan precursors from flaxseed. Nutr Cancer, 26: 159–165, 1996a.

Thompson L U, Rickard S E, Orcheson L J and Seidl M M: Flaxseed and its lignan and oil components reduce mammary tumor growth at a late stage of carcinogenesis. Carcinogenesis, 17: 1373–1376, 1996b.

Tou J C L, Chen J and Thompson U. Flaxseed and its lignan precursor, secoisolariciresinol diglycoside, affect pregnancy outcome and reproductive development in rats. J Nutr, 128: 1861–1868, 1998.

Wang C, Mäkelä T, Hase T, Adlercreutz H and Kurzer M S: Lignans and flavonoids inhibit aromatase enzyme in human adipocytes. J Steroid Biochem Molec Biol, 50: 205–212, 1994.

Waters A P and Knowler J T. Effect of a lignan (HPMF) on RNA synthesis in the rat uterus. J Reprod. Fert, 66:379–381, 1982.

Zhang J-X, Hallmans G, Landström M, Bergh A, Damber J-E, Åman P and Adlercreutz H. soy and rye diets inhibit the development of Dunning R3327 prostatic adenocarcinoma in rats. Cancer Letters, 114: 313–314, 1997.

The invention claimed is:

1. A food product comprising an effective amount of an active agent which is hydroxymatairesinol, a geometric isomer or stereoisomer thereof, or an acceptable salt thereof, or a mixture thereof, wherein the food product is selected from the group consisting of a nutritional supplement and a nutrient.

2. The food product of claim 1, wherein said active agent has been derived from coniferous wood.

* * * * *